United States Patent [19]  
Julia

[11] 3,970,706  
[45] July 20, 1976

[54] PROCESS FOR SYNTHESIZING CIS-α-SANTALENE AND CIS-α-SANTALOL

[75] Inventor: Marc Julia, Paris, France

[73] Assignee: Agence Nationale de Valorisation de la Recherche (ANVAR), Neuilly-sur-Seine, France

[22] Filed: Aug. 22, 1973

[21] Appl. No.: 390,490

[30] Foreign Application Priority Data

Aug. 25, 1972 France .............................. 72.30302

[52] U.S. Cl. ........................ 260/617 F; 260/488 B; 260/607 A; 260/631.5; 260/666 PY
[51] Int. Cl.² ................ C07C 33/05; C07C 147/08; C07C 69/145
[58] Field of Search ......... 260/617 F, 607 A, 631.5, 260/488 B Primary Examiner—Alton D. Rollins
Assistant Examiner—D. B. Springer
Attorney, Agent, or Firm—Christie, Parker & Hale

[57] ABSTRACT

The invention relates to a process for the grafting a chain on to the 10-position carbon atom of a tricyclene skeleton, more particularly for producing 10-substituted stereospecific tricyclenes, especially cis-α-santalene and cis-α-santalol. The process involves the production of a sulphone of the tricyclene, the reaction of the sulphone with the halogenated derivative of the desired side chain and desulphonating the product.

3 Claims, No Drawings

PROCESS FOR SYNTHESIZING CIS-α-SANTALENE AND CIS-α-SANTALOL

This invention relates to a general stereospecific process for grafting a chain onto the 10-position carbon atom of a tricyclene skeleton and, more particularly, to a process for synthesising cis-α-santalene and cis-α-santalol.

α-Santalene and α-santalol are two constituents of the essence of *Santalum album* which has a tricyclene skeleton and which can be represented by the following general formula:

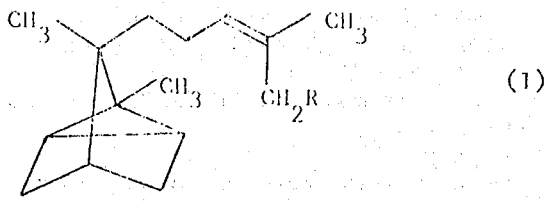

in which, where R = H, it represents α-santalene whilst, where R = OH, it represents α-santalol.

BACKGROUND OF THE INVENTION

α-Santalene has been synthesised from π-bromotricyclene by converson into Grignard's compound followed by condensation with dimethylallyl mesitoate (E. J. Corey, S. W. Chow and R. A. Scherrer, J. Amer. chem. Soc., 1957, 79, 5773) or by extension of the chain in several stages (S. Y. Kamat, K. K. Chakravarti and S. C. Bhattacharyya, Tetrahedron, 1967, 23, 4487) or by the condensation of π-iodotricyclene with π-dimethylallyl nickel (E. J. Corey and M. F. Semmelhack, J. Amer. chem. Soc., 1967, 89, 2755).

α-Santalol has been synthesised by oxidising α-santalene with selenium oxide (V. M. Sathe, M. V. Kadival, K. K. Chakravarti and S. C. Bhattacharyya, Indian J. Chem., 1964, 4, 393) or from π-bromotricyclene by building the chain in several stages (J. Colonge, G. Descotes, J. Bahurel and A. Menet, Bull. Soc. chim. France, 1966, page 374; S. Y. Kamat, K. K. Chakravarti and S. C. Bhattacharyya, Tetrahedron, 1967, 23, 4487; R. G. Lewis, D. H. Gutstavon and W. F. Erman, Tet. Letters, 1967, 401). These syntheses are not stereoselective.

The function carried by the terminal carbon atom of the chain appears in the cis- and in the trans-position. E. J. Corey et al. introduced new methods for synthesising cis-allyl alcohols and were successful in preparing α-santalol by stereoselective syntheses.

SUMMARY OF THE INVENTION

In addition to being easier to carry out than the processes described above, the new process for preparing tricyclene compounds with a chain on the 10-position carbon atom has the advatage that synthesis of the chain is carried out separately with the result that it is possible to place substituents of known stereochemistry on this chain without having in any way to involve the tricyclene skeleton.

In addition, the process according to the invention retains the stereochemistry of the chain after it has been grafted.

The process according to the invention comprises the following stages:

1. converting a π-halotricyclene into phenylsulphone by the action of sodium benzene sulphinate which enables the α-carbon atom to be anionised;
2. condensing on this α-carbon atom a suitably prefabricated halogenated chain ("synthons") through the halogen atom;
3. subsequently carrying out a desulphonating reduction to obtain the tricyclene compound having a chain grafted onto its 10-position carbon atom, the stereochemistry of this chain having been kept intact.

In one embodiment of stage 1, the compounds are reacted in dimethyl formamide (DMF) and, in a preferred embodiment of the invention for this stage 1, the starting product is π-bromotricyclene and the reaction is carried out in DMF at a temperature of around 150°C.

In a first embodiment of stage 2, the reaction takes place in the presence of butyl lithium and tetramethyl ethylene diamine (TMED) in a solvent.

In a second embodiment of stage 2, butyl lithium is used in the present of HMPT (hexamethyl phosphortriamide) in a solvent. The HMPT is preferably present in a quantity representing 20% of the solvent.

The preferred solvent for this stage is tetrahydrofuran (THF).

Although it enables various "Synthons" to be grafted onto a tricyclene skeleton, the process according to the invention is suitable above all for synthesising α-santalene and α-santalol in the cis-form. In this case, a "synthon" of the formula

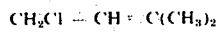

is preferably used for synthesising α-santalene during stage 2, whilst a "synthon" of the formula

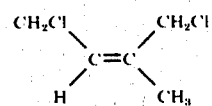

in the cis-form is preferably used for synthesising cis-α-santalol. This stereochemistry of the chain will be retained in the end product, one of the chlorine atoms having enabled it to be grafted onto the anionised α-carbon atom of the phenyl nucleus, the other chlorine atom having been replaced by a hydroxyl function by any known method.

One known and preferred method of replacing the chlorine atom by a hydroxy radical after grafting of the chain onto the sulphone is to treat the resulting compound with sodium acetate to obtain the acetic ester of 10-phenylsulphonyl-α-santalol. In stage 3 of the process, namely the desulphonating reduction, this ester function is converted into an alcohol function by reduction at the same time as desulphonation.

In one embodiment of stage 3 of the process according to the invention, the desulphonating reduction is carried out in the presence of a sodium amalgam in a solvent, especially ethanol.

When carrying out this embodiment of stage 3 of the process for preparing α-santalene, it was qualitatively found that another compound whose structure is probably that of 10,11-dehydro-α-santalene is formed alongside the required compound. Accordingly, a preferred embodiment of stage 3 of the process according to the invention comprises for carrying out the desulphonating reduction with sodium amalgam in HMPT containing 10% of ethanol.

During synthesis of the cis-α-santalol, it is necessary to react a cis-halogenated "synthon". One method of preparing a "synthon" of this kind will be described hereinafter, although the invention is by no means confined to this particular method.

3-methyl-2-butene lactone is prepared by the action of senecioic acid on N-bromosuccinimide. The lactone is reduced with lithium aluminohydride to form 2-methyl-2-butene-1,4-diol. The cis-glycol is then treated by Meyers and Collington's method (A. J. Meyers and E. W Collington, Tetrah. 1971, 27, 5979) to form the cis-dichloride.

As an example of the application of the grafting process according to the invention, a synthesis of α-santalene and cis-α-santalol will be described hereinafter although the invention is by no means limited to this particular synthesis and modifications may be made to the syntheses described without departing from the scope of the invention.

DESCRIPTION OF PREFERRED EMBODIMENTS

In the following Examples, the chromatograms were prepared with silica gel using a 1 : 4 ether : pentane mixture.

The figures in brackets relate to the general synthesis scheme.

EXAMPLE 1 — Synthesis of α-santalene

A. Synthesis of π-phenylsulphonyl tricyclene (2)

(−) π-bromotricyclene (1) is prepared from (+) α-bromocamphor by Corey's method.

12 g of sodium benzene sulphinate (73 m mol) and 8.6 g of (−) π-bromotricyclene (40 m mol) in 100 cc of anhydrous DMF are heated under reflux (153°C) for 9 hours. After cooling, the mixture is poured into 300 cc of an aqueous 80% saturated NaCl solution and extracted 3 times with ether (300 + 2 × 200 cc). The extracts are washed twice with a saturated NaCl solution (2 × 200 cc), dried over MgSO$_4$ and evaporated.

The residue crystallises in the form of colourless needles by the addition of hexane.

The yield comprises 6.3 g (57%) of a product identified with π-phenylsulphonyl tricyclene and having the following characteristics:

Mp = 98°C; single spot in chromatography ($R_f$ = 0.5);

MS molecular peak at 276;

NMR (δ) 0.91, 0.98, 1.07, 1.14, 1.26, 1.63, 1.82, 2.31 (s ; 13 H) 3.07 (wide S ; 2 H), 7.55 (m complex ; 3 H) 7.90 (m complex ; 2 H).

B. Synthesis of 10-phenylsulphonyl-α-santalene (3)

0.29 ml of a solution of butyl lithium in hexane (0.535 m mol) is added dropwise under nitrogen over a period of 2 minutes at −78°C (CO$_2$ :acetone mixture) to a stirred solution of π-phenylsulphonyl tricyclene obtained in accordance with (A) (138 mg), (0.5 m mol) containing 0.4 ml of HMPT in 1.6 ml of THF.

The orange-coloured solution is heated for 30 minutes to 0°C and then cooled to −78°C. This is followed by the addition of 78 mg of 3-methyl-1-chloro-2-butene (0.74 m mol), after which the temperature is allowed to return to 0°C. After 30 minutes, the colour has turned pale and stirring is continued for 30 minutes. The solution is then poured into an aqueous NaCl solution and extracted with ether. The ethereal phase is washed three times with water, dried and evaporated to give a yellowish oil.

A colourless viscous oil which does not crystallise is isolated in a yield of 165 mg (96%) by preparative thin-layer chromatography.

The chromatogram shows the presence of a trace of the starting product.

The product obtained, 10-phenylsulphonyl-α-santalene (3), is identified by its spectrum:
- NMR (δ) 1.07, 1.17, 1.32, 1.35, 1.44 (maxima of a massive complex ; 16 H); 1.6–2.1 (massive complex ; 2H) ; 2.25–2.9 (massive complex ; 3 H) ; 3.18 (m; 1 H) ; 4.33 (m ; 1 H) ; 7.5 (m ; 3 H) ; 7.8 (m ; 2 H), Mass spectrum: m/e 344 (M$^+$), 203 (M$^+$-SO$_2$Ph), 202 (M$^+$-HSO$_2$ Ph), 121 (M$^+$-(CH$_3$)$_2$C:CHCH$_2$CHSO$_2$Ph), 77 (Ph$^+$), 60 ($^+$CH$_2$CH:C (CH$_3$)$_2$).

C. Synthesis of α-santalene (4) and 10,11-dehydro-α-santalene (5)

In ethanol:

A solution containing 380 mg of 10-phenylsulphonyl-α-santalene obtained in accordance with (B) above in 12 ml of absolute ethanol is added to 12 g of a 6% sodium amalgam in powder form. The mixture is then stirred under nitrogen for 1 hour at a temperature of 0°C. It is then poured into water, extracted and the residue washed with a 1 : 1 ether : pentane mixture. The extracts are washed with water, dried and evaporated. 226 mg of a colourless oil are obtained, being separated by preparative chromatography (benzene : hexane 1 : 2) into:

. α-santalene (4) : 154 mg, 67.5%, identified by its infrared spectrum by comparison with the data in the literature; its mass spectrum : molecular peak at 204 and its NMR spectrum (δ) 0.80, 0.98, 1.11, 1.21, 1.28 (maxima of a massive complex ; 12 H), 1.57, 1.65, 1.79, 1.95, 2.07 (maxima of a massive complex ; 11 H), 5.04 (t, J=7 Hz ; 1 H) ; and . 10,11-dehydro-α-santalene (5) : 68 mg, 30.5%, UV spectrum λmax 240 nm (∈ = 10$^4$), MS : molecular peak at 202, IR (cm$^{-1}$) : 1693, 1620, 988, 965

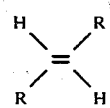

872, 855

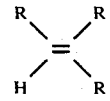

NMR spectrum : (δ) 0.92, 1.06 (s), 0.7–1.4 (massive complex ; 10 H with s) 1.73 (wide s) 1.4–2.0 (massive complex; 9 H with s) 5.32, 5.57, 5.77, 5.95, 6.11, 6.20, 6.38 (maxima of a multiplet ABC ; 3 H).

In a mixture of HMPT and ethanol:

Samples of 50 mg of 10-phenylsulphonyl-α-santalene are reduced with sodium amalgam (1 g) in a mixture of HMPT and ethanol (1.5 ml) by the method described above. The crude products are extracted by extraction and the ratio of α-santalene to dehydro-α-santalene is evaluated by chromatography (10% SE 30 ; 130°C).

| % (vol) EtOH | % α-santalene | % dehydro-α-santalene |
|---|---|---|
| 40 | 68.5 | 31.5 |
| 20 | 83.5 | 16.5 |
| 14.7 | 84.6 | 15.4 |
| 10 | 85 | 15.1 |
| 2.2 | 54 | 46 |

EXAMPLE 2 — Synthesis of α-santalol

A. Synthesis of cis-14-chloro-10-phenylsulphonyl-α-santalene (6)

π-phenylsulphonyl tricyclene is prepared in the same way, under the same conditions and in the same quantity as in (A) of Example 1. Following the addition of HMPT, THF and butyl lithium under the same conditions as at the beginning of (B) of Example 1, cis-1,4-dichloro-2-methyl-2-butene is added in a quantity of 97 mg (0.695 m mol) at a temperature of −78°C. The mixture is heated to between −5° and −20°C, and the orange-colour of the solution turns pale within 1 to 2 hours. The solution is left to return to ambient temperature, after which it is poured into an aqueous saturated NaCl solution. This is followed by extraction with ether, the extract being washed with water, dried and evaporated.

173 mg (92% yield) of a single product, namely cis-14-chloro-10-phenylsulphonyl-α-santalene, are obtained by thin-layer chromatography.

The NMR-spectrum is too complex to be interpreted. The mass spectrum does not have a molecular peak at 378, the heaviest peak being at 343 (M'-Cl).

This compound is identified from its conversion into α-santalol in the following stages.

B. Synthesis of 10-phenylsulphonyl-α-santalol acetate (7)

110 mg of the chloride (6) in 0.5 cc of DMF are heated for 5.5 hours to 70°C with 50 mg of dry sodium acetate in excess. After cooling, the product is poured into water saturated with NaCl. This is followed by extraction with ether, the extracts being washed, dried and evaporated. According to its chromatogram (ether-pentane 3 : 7), the clear yellow oil obtained contains a trace of phenylsulphonyl tricyclene alongside the quasi-exclusive constituent (111 mg ; 95%).

The NMR spectrum is complex (δ) 2.00 (s ; 3 H ; CH₃ CO—). Mass spectrum: peaks at 402 (molecular) and 342 (M'- AcOH).

C. Synthesis of α-santalol (8)

A solution of 82 mg of the sulphone acetate (7) previously obtained in HMPT (1.8 cc) and ethanol (0.3 cc) is added to 1.4 g of 6% sodium amalgam in powder form, followed by rapid stirring under nitrogen for 1 hour at 0°C. Following the procedure described above, the main product is isolated by chromatography (ether : petroleum ether 1 : 3), Rf = 0.44 (36 mg ; 80%), and is identified with a sample of authentic α-santalol prepared by preparative chromatography in the vapour phase from a sample of α+β santalol, and by comparison of its IR and NMR spectra as quoted in the literature; $(\alpha)_D^{25} = +16.1°$; literature : natural product ; $(\alpha)_D^{25} = +17.0°$; synthetic product : + 17.5°.

The mass spectrum shows peaks at 220 (molecular), 203 (M'-OH), 202 (M'-H₂O) and 187 (M'-H₂O-CH₃). A trace of 10,11-dehydro-α-santalol is suggested by the peak at 218. Chromatography on silica gel impregnated with silver nitrate indicates a trace of an impurity (<3%).

What is claimed is:

1. Process for the preparation of cis α-santalol comprising the following stages:
   a. treating π-bromotricyclene with sodium benzene sulphinate in dimethylformamide to form the corresponding phenylsulphone;
   b. treating the phenylsulphone obtained in stage (a) in presence of butyl lithium in a mixture of tetrahydrofuran/HMPT or THF/tetramethylethylene diamine with the cis 1, 4-dichloro-2-methyl-2-butene to form a compound corresponding to the following formula:

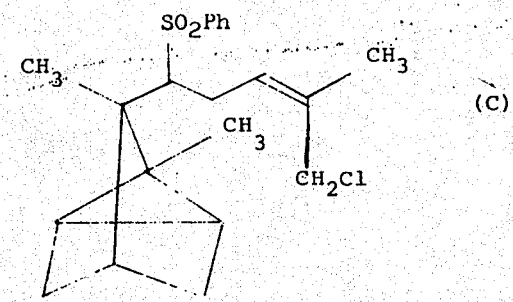

(C)

c. the compound (C) is treated with sodium acetate in dimethylformamide to form a compound corresponding to the following formula:

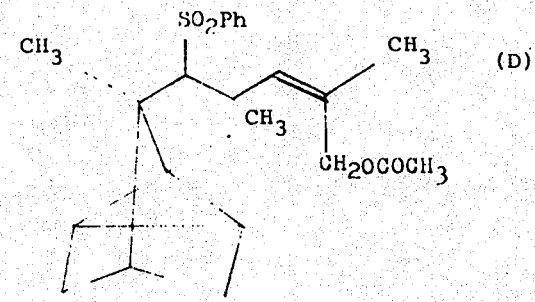

(D)

d. the compound obtained in stage (c) is treated with sodium amalgam to form the compound cis α-santalol.

2. A process according to claim 1 wherein stage (d) is conducted in a solvent chosen from the group consisting of ethanol and a mixture of HMPT and ethanol.

3. A process for the preparation of cis α-santalol comprising the following stages:
   a. treating π-bromotricyclene with sodium benzene sulphinate in DMF at around 150°C;
   b. treating the phenylsulphone obtained in stage (a) in a mixture of butyl lithium, HMPT and THF with the cis 1,4-dichloro-2-methyl-2-butene;
   c. treating cis 14-chloro-10-phenylsulphonyl-α-santalene obtained in stage ((b) with sodium acetate in DMF;
   d. treating the compound obtained in stage (c) with sodium amalgam in HMPT and ethanol.

* * * * *